Figure 3:
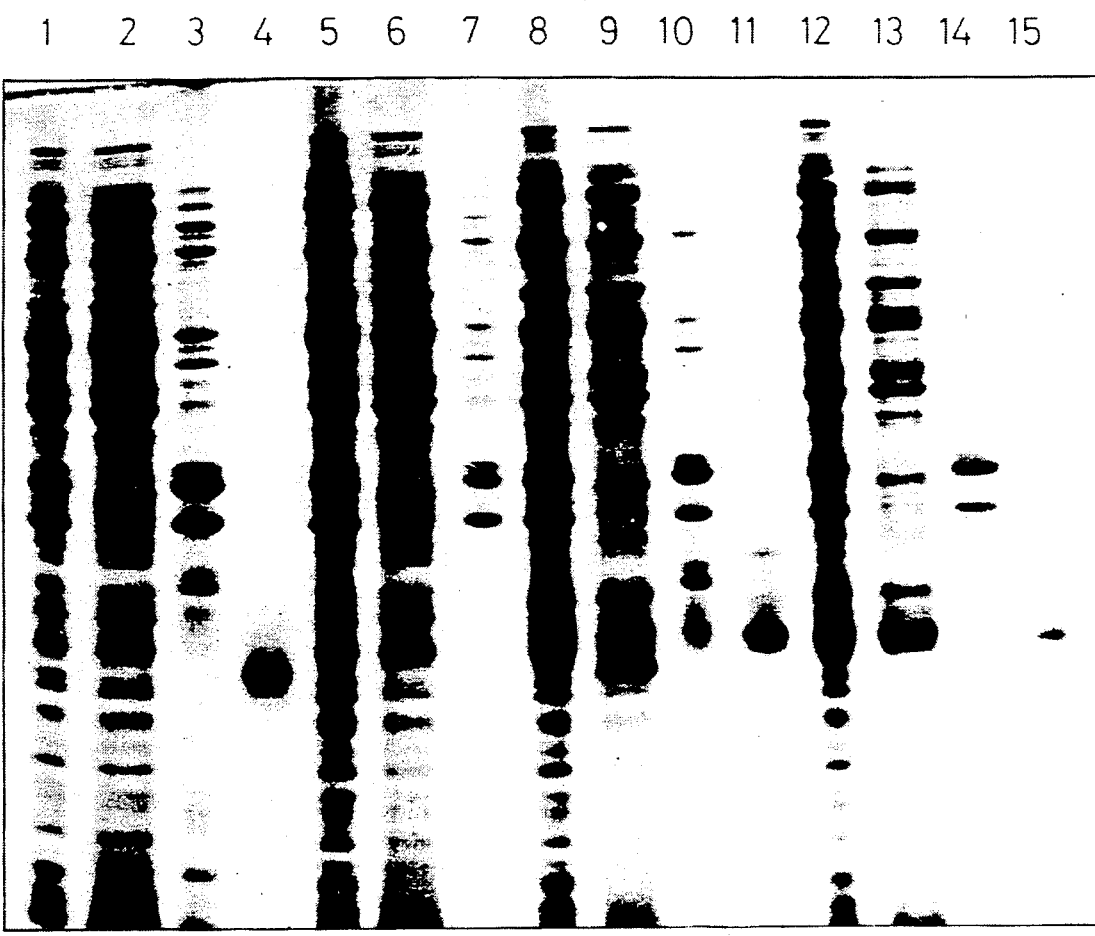

United States Patent [19]
Bennett et al.

[11] Patent Number: 5,093,241
[45] Date of Patent: Mar. 3, 1992

[54] C-TERMINAL CAT FUSION PROTEIN AND PROCESS OF PREPARATION BY RECOMBINANT DNA

[75] Inventors: Alan D. Bennett; Stephen K. Rhind; Peter A. Lowe, all of Berkshire; Christopher C. G. Hentschel, London, all of United Kingdom

[73] Assignee: Celltech, Ltd., Berkshire, England

[21] Appl. No.: 250,962

[22] Filed: Sep. 23, 1988

Related U.S. Application Data

[63] Continuation of Ser. No. 690,488, filed as PCT/GB84/00179, May 24, 1984, abandoned.

[30] Foreign Application Priority Data

May 24, 1983 [GB] United Kingdom ............ 8314362

[51] Int. Cl.$^5$ .............. C07H 15/12; C12P 21/00; C12P 21/02
[52] U.S. Cl. .................. 435/69.4; 435/69.1; 435/252.33; 435/320.1; 536/27; 935/47; 935/48; 935/49; 935/51
[58] Field of Search ............ 435/68, 70, 172.3, 253, 435/320.1, 252.33, 252.3, 69.1, 69.4, 172.3; 935/47, 48, 49, 51; 536/27

[56] References Cited

U.S. PATENT DOCUMENTS 4,411,994 10/1983 Gilbert et al. ................ 435/71

FOREIGN PATENT DOCUMENTS 0035384 9/1981 European Pat. Off. .
70675 1/1983 European Pat. Off. ............ 435/68

OTHER PUBLICATIONS

Idida et al., *EMBO J.* vol. 1 (6) pp. 755-759 1982, "Pnenotypic Reversion of an IS1-Mediated Deletion Mutation: A Combined Role for Point Mutations ...".
Nishimori et al., *Gene* vol. 19 (3) pp. 337-347, 1982.
Uhler et al., *J. Biol Chem.*, vol. 258 (1) pp. 257-261.
Goldfarb, D. S. et al., "Translational Block To Expression ...", *Proc. Natl. Acad. Sci.* U.S.A. 79:5886-5890, 1982.
Schroder, J. et al., "Experssion Of Plant Tumor-Specific Proteins . . . ", *Nucleic Acids Research* 9(20):5187-5202 1981.
*Enzyme Nomenclature* Academic Press, NY 1979 pp. 324-325 and 330-331.
Goldfarb, D. S. et al., In:Ganesan, A. T., et al., eds *Molecular Cloning and Gene Regulation In Bacilli* Academic Press, NY, 1982 pp. 311-324.

*Primary Examiner*—Robin L. Teskin
*Attorney, Agent, or Firm*—Cushman, Darby & Cushman

[57] ABSTRACT

A process for the production of a fusion protein comprising an active portion of a chloramphenicol acetyltransferase (CAT) protein and a polypeptide. The fusion protein may be purified using CAT substrate affinity chromatography. The eucaryotic polypeptide may be calcitonin or a dervative thereof such as calcitoninglycine. Other polypeptides described include enzymes such as chymosin, prochymosin and preprochymosin, hormones such as ACTH, insulins, and growth hormones and antigenic polypetides such as foot and mouth disease virus antigenic polypetide. The fusion protein may be cleaved at a site susceptible to selective enzymic or chemical cleavage to produce free polypeptide. The fusion protein may be used as an immunogen.

22 Claims, 12 Drawing Sheets

```
                                         ScaI
                                          ↓
Native      5'..............  CAG TAC TGC GAT GAG TGG CAG GGC GGG GCG
                              Gln Tyr Cys Asp Glu Trp Gln Gly Gly Ala ScaI
                                          ↓
EDR104      5'..............  CAG TAC TGC GGT AAT GAC TCC AAC TTA TTG
                              Gln Tyr Cys Gly Asn Asp Ser Asn Leu Leu ScaI                    BglII
                                          ↓                        ↓
pAB7        5'..............  CAG TAC TGC GGT AAT GAC TCT CAG ATC TGG
                              Gln Tyr Cys Gly Asn Asp Ser Gln Ile Trp ScaI
                                          ↓
pAB8        5'..............  CAG TAC TGC GGT AAT GAC TCC AAC TTA TTG
                              Gln Tyr Cys Gly Asn Asp Ser Asn Leu Leu ScaI                    BglII
                                          ↓                        ↓
pAB19       5'..............  CAG TAC TGC GGT AAT GAC TCC ATC AGA TCT
                              Gln Tyr Cys Gly Asn Asp Ser Ile Arg Ser ScaI
                                          ↓
pCT201 (from pAB8)5'...       CAG TAC TGC GGT AAT GAC TCC AAC TTA TTG
                              Gln Tyr Cys Gly Asn Asp Ser Asn Leu Leu ScaI                    BglII
                                          ↓                        ↓
pCT202 (from pAB19)5'..       CAG TAC TGC GGT AAT GAC TCC ATC AGA TCT
                              Gln Tyr Cys Gly Asn Asp Ser Ile Arg Ser ScaI                    BglII
                                          ↓                        ↓
pCT203 (from pAB7)5'...       CAG TAC TGC GGT AAT GAC TCT CAG ATC TGG
                              Gln Tyr Cys Gly Asn Asp Ser Gln Ile Trp ScaI
                                          ↓
pAB74       5'..............  CAG TAC TGC GGT AAT CTG AGT ACT TGC ATG
(from pAB7)                   Gln Tyr Cys Gly Asn Leu Ser Thr Cys Met ScaI                    BglII
                                          ↓                        ↓
pCT2023     5'.............   CAG TAC TGC GGT AAT GAC TCC ATC AGA TCT
(from pCT202)                 Gln Tyr Cys Gly Asn Leu Ser Ile Arg Ser ScaI                    BglII
                                          ↓                        ↓
pCT2024     5'..............  CAG TAC TGC GGT AAT GAC TCC ATC AGA TCT
(from pCT202)                 Gln Tyr Cys Gly Asn Leu Ser Ile Arg Ser ScaI                    BglII
                                          ↓                        ↓
pCT2025     5'..............  CAG TAC TGC GGT AAT GAC TCC ATC AGA TCT
(from pCT2023)                Gln Tyr Cys Gly Asn Leu Ser Ile Arg Ser ScaI                    BglII
                                          ↓                        ↓
pCT2026     5'..............  CAG TAC TGC GGT AAT GAC TCC ATC AGA TCT
(from pCT2024)                Gln Tyr Cys Gly Asn Leu Ser Ile Arg Ser
```

Fig. 1(i)

TAA .... 3' (Alton and Vapnek, 1979) 219 Amino-acids
End

Tth111I
```
                                                  ↓
ATA GTG TTT TAT GTT CAG ATA ATG CCC GAT GAC TTT GTC ATG CAG CTC
Ile Val Phe Tyr Val Gln Ile Met Pro Asp Asp Phe Val Met Gln Leu

Sst1 Bgl2
     ↓    ↓
AGC TCC AGA TCT GAA GCT CCA CCG ATT TTG AGA ACG ACA GCG ACT TCC
Ser Ser Arg Ser Glu Ala Pro Pro Ile Leu Arg Thr Thr Ala Thr Ser

Bgl2           Sst1 Bgl2
   ↓              ↓    ↓
TCA GAT CTG GAG CTC CAG ATC TGA .... 3' 226 Amino-acids
Ser Asp Leu Glu Leu Gln Ile End Sst1 Bgl2
        ↓    ↓
GGA GCT CCA GAT CTG ACC GTC CCA GCC GTG CCA GGT GCT GCC TCA GAT
Gly Ala Pro Asp Leu Thr Val Pro Ala Val Pro Gly Ala Ala Ser Asp Bgl2      EcoR1    HindIII
   ↓          ↓        ↓
TCA GAT CTG GAA TTC AAG CTT GGC TGC CAA AGC CGC AAG GAA TTT ACC
Ser Asp Leu Glu Phe Lys Leu Gly Cys Gln Ser Arg Lys Glu Phe Thr EcoR1    HindIII
 ↓         ↓
GAA TTC AAG CTT GGC TGC CAA AGC CGC AAG GAA TTT ACC AAC CTT CTT
Glu Phe Lys Leu Gly Cys Gln Ser Arg Lys Glu Phe Thr Asn Leu Leu EcoR1 Hind111
 ↓      ↓
AAT TCA AGC TTG GCT GCC AAA GCC GCA AGG AAT TTA CCA ACC TTC TTA
Asn Ser Ser Leu Ala Ala Lys Ala Ala Arg Asn Leu Pro Thr Phe Leu Sph1
 ↓
CTG GGC ACA TAC ACG CAG GAC TTC AAC AAG TTT CAC ACG TTC CCC CAA
Leu Gly Thr Tyr Thr Gln Asp Phe Asn Lys Phe His Thr Phe Pro Gln Sph1
                               ↓
AAG CGG TGC GGT AAT CTG AGT ACT TGC ATG CTG GGC ACA TAC ACG CAG
Lys Arg Cys Gly Asn Leu Ser Thr Cys Met Leu Gly Thr Tyr Thr Gln Sph1
                               ↓
AAG CGG TGC GGT AAT CTG AGT ACT TGC ATG CTG GGC ACA TAC ACG CAG
Lys Arg Cys Gly Asn Leu Ser Thr Cys Met Leu Gly Thr Tyr Thr Gln Acc1         Sph1
             ↓            ↓
GAA TGT GGC AAC CTG TCT ACT TGC ATG CTG GGC ACA TAC ACG CAG GAC
Glu Cys Gly Asn Leu Ser Thr Cys Met Leu Gly Thr Tyr Thr Gln Asp Acc1         Sph1
             ↓            ↓
GAA TGT GGC AAC CTG TCT ACT TGC ATG CTG GGC ACA TAC ACG CAG GAC
Glu Cys Gly Asn Leu Ser Thr Cys Met Leu Gly Thr Tyr Thr Gln Asp
```

Fig. 1(ii)

```
CAC CGA TTT TGA .... 3' (Iida et al 1982) 238 Amino-acids
His Arg Phe End

GTC CCA GCC GTG CCA GGT GCT GCC TCA GAT TCA GGT TAT GCC GCT CAA
Val Pro Ala Val Pro Gly Ala Ala Ser Asp Ser Gly Tyr Ala Ala Gln

TCA GGT TAT GCC GCT CAA TTC GCT GCG TAT ATC GCT TGC TGA .... 3'
Ser Gly Tyr Ala Ala Gln Phe Ala Ala Tyr Ile Ala Cys End

AAC CTT CTT AAA CAT AAA GTG TCT CCT TAT AAA CGC AGA AAG GCC CAC
Asn Leu Leu Lys His Lys Val Ser Pro Tyr Lys Arg Arg Lys Ala His

AAA CAT AAA GTG TCT CCT TAT AAA CGC AGA AAG GCC CAC CCG AAG GTG
Lys His Lys Val Ser Pro Tyr Lys Arg Arg Lys Ala His Pro Lys Val

AAC ATA AAG TGT CTC CTT ATA AAC GCA GAA AGG CCC ACC CGA AGG TGA
Asn Ile Lys Cys Leu Leu Ile Asn Ala Glu Arg Pro Thr Arg Arg End

ACT GCA ATT GGG GTT GGA GCA CCT GGT TGA .... 3' 243 Amino-acids
Thr Ala Ile Gly Val Gly Ala Pro Gly End GAC TTC AAC AAG TTT CAC ACG TTC CCC CAA ACT GCA ATT GGG GTT GGA
Asp Phe Asn Lys Phe His Thr Phe Pro Gln Thr Ala Ile Gly Val Gly GAC TTC AAC AAG TTT CAC ACG TTC CCC CAA ACT GCA ATT GGG GTT GGA
Asp Phe Asn Lys Phe His Thr Phe Pro Gln Thr Ala Ile Gly Val Gly TTC AAC AAG TTT CAC ACG TTC CCC CAA ACT GCA ATT GGG GTT GGA GCA
Phe Asn Lys Phe His Thr Phe Pro Gln Thr Ala Ile Gly Val Gly Ala TTC AAC AAG TTT CAC ACG TTC CCC CAA ACT GCA ATT GGG GTT GGA GCA
Phe Asn Lys Phe His Thr Phe Pro Gln Thr Ala Ile Gly Val Gly Ala
```

Fig. 1(iii)

```
TTC GCT GCG TAT ATC GCT TGC TGA .... 3' 258 Amino-acids
Phe Ala Ala Tyr Ile Ala Cys End
```

248 Amino-acids

```
CCG AAG GTG AGC CAG TGT GAT TAC ATT TTC TCT TGA .... 3' 202
Pro Lys Val Ser Gln Cys Asp Tyr Ile Phe Ser End      Amino-acids
```

```
AGC CAG TGT GAT TAC ATT TTC TCT TGA .... 3' 259 Amino-acids
Ser Gln Cys Asp Tyr Ile Phe Ser End
```

.... 3' 250 Amino-acids

<u>Mst2</u>

```
GCA CCT TAG .... 3' 252 Amino-acids
Ala Pro End
```

```
GCA CCT GGT TGA .... 3' 253 Amino-acids
Ala Pro Gly End
```

```
CCT TAG .... 3' 252 Amino-acids
Pro End
```

```
CCT GGT TGA .... 3' 253 Amino-acids
Pro Gly End
```

Fig. 1(iv)

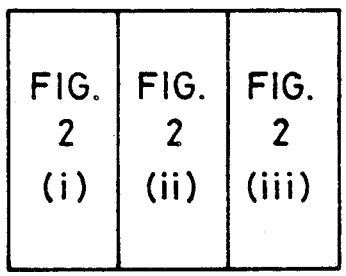
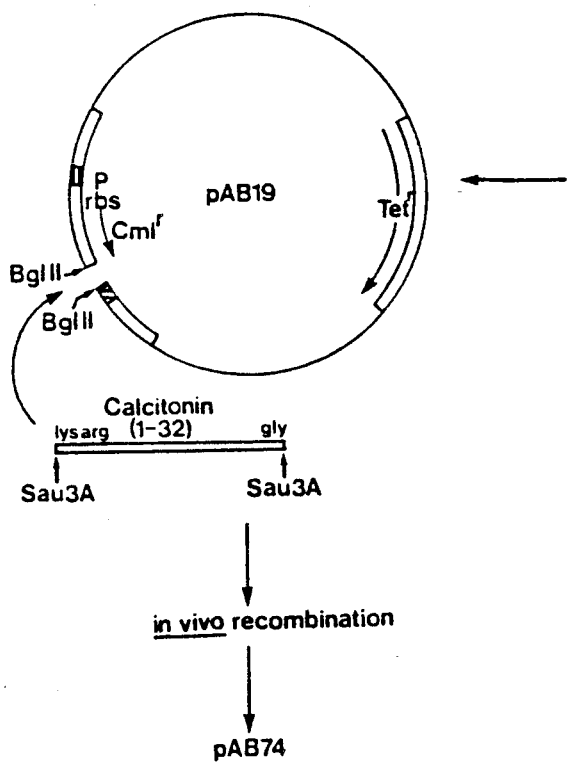
Fig. 2(i)

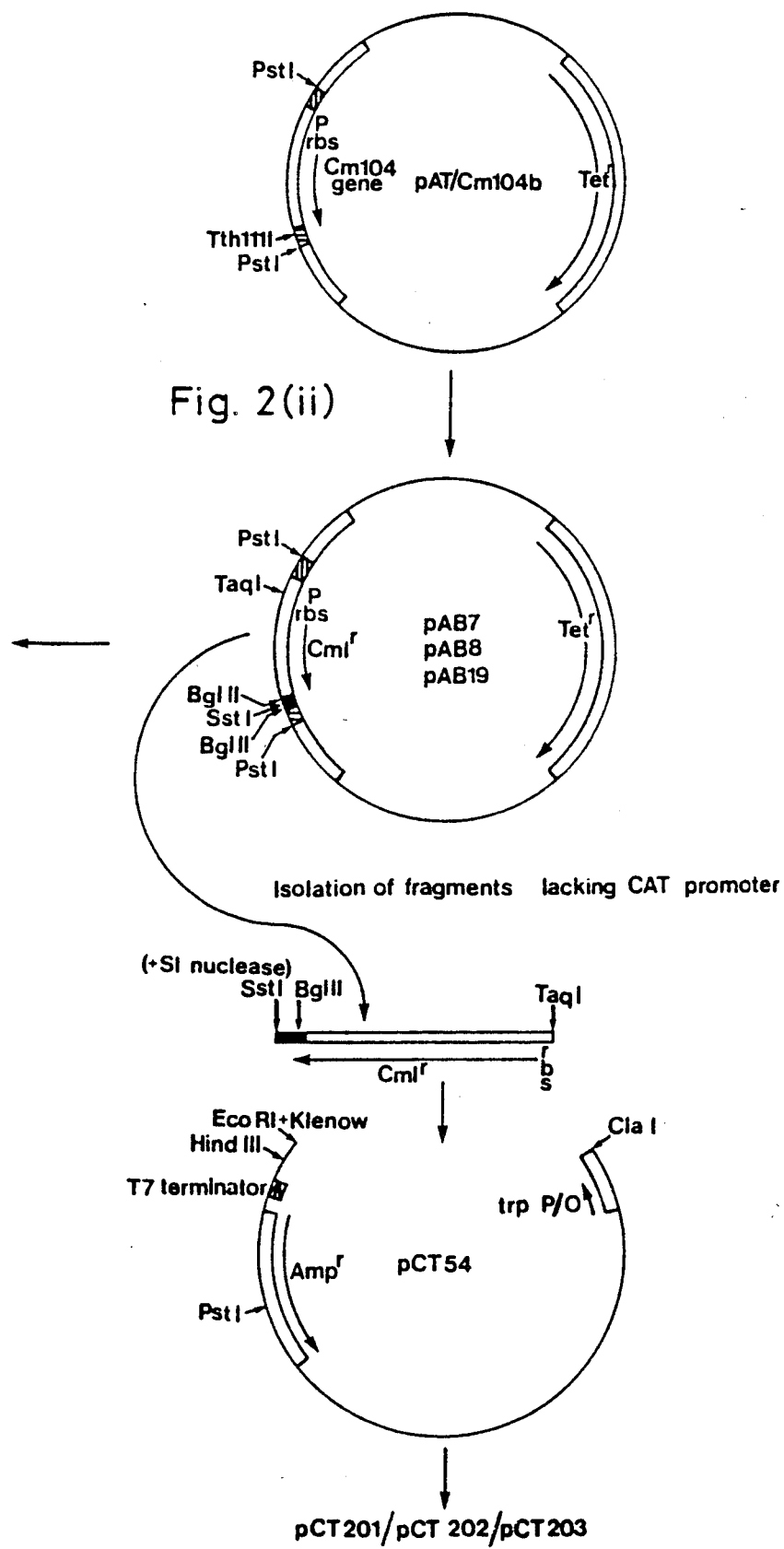

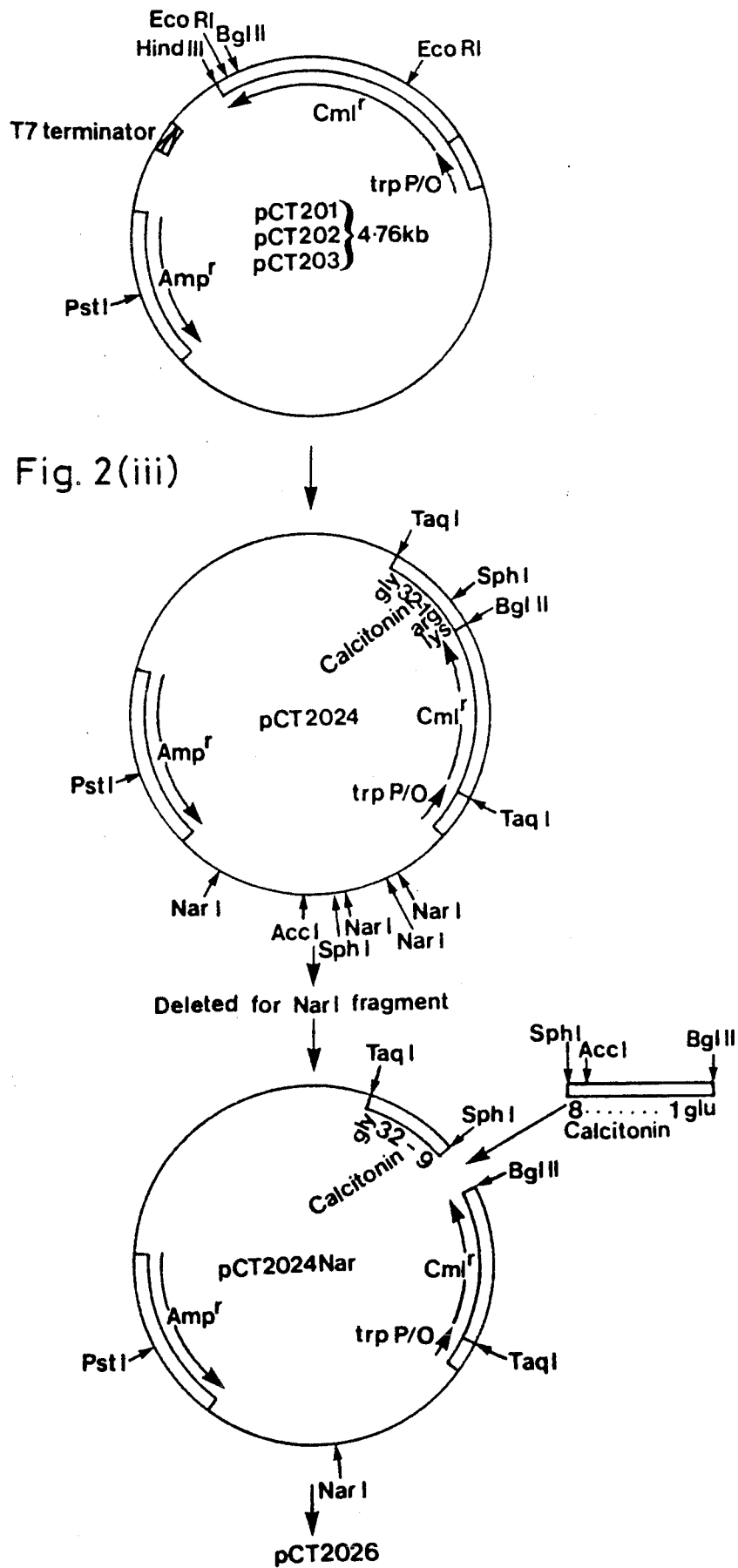
Fig. 2(iii)

FIG. 6
A. CHEMICALLY SYNTHESIZED hCT
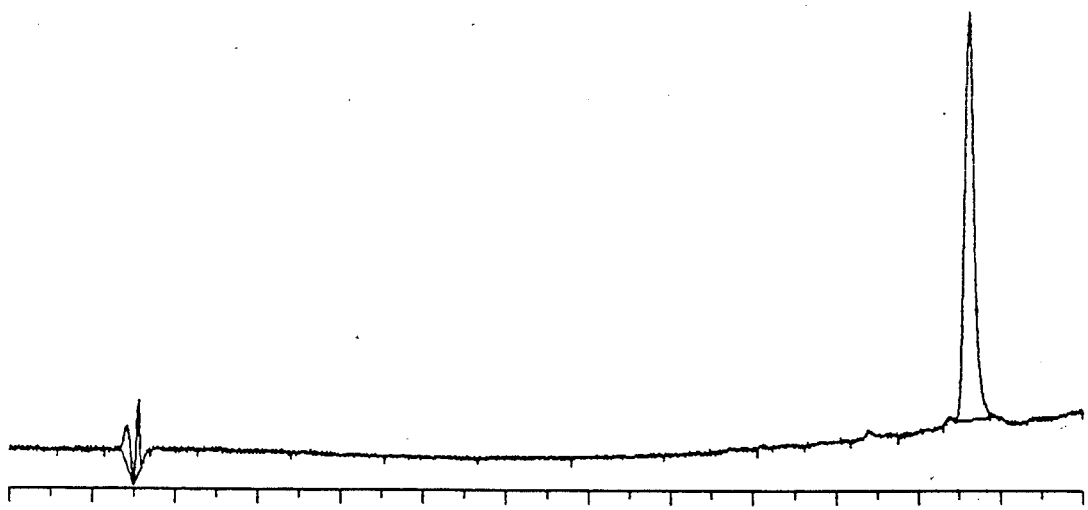
B. RECOMBINANT hCT-GLY
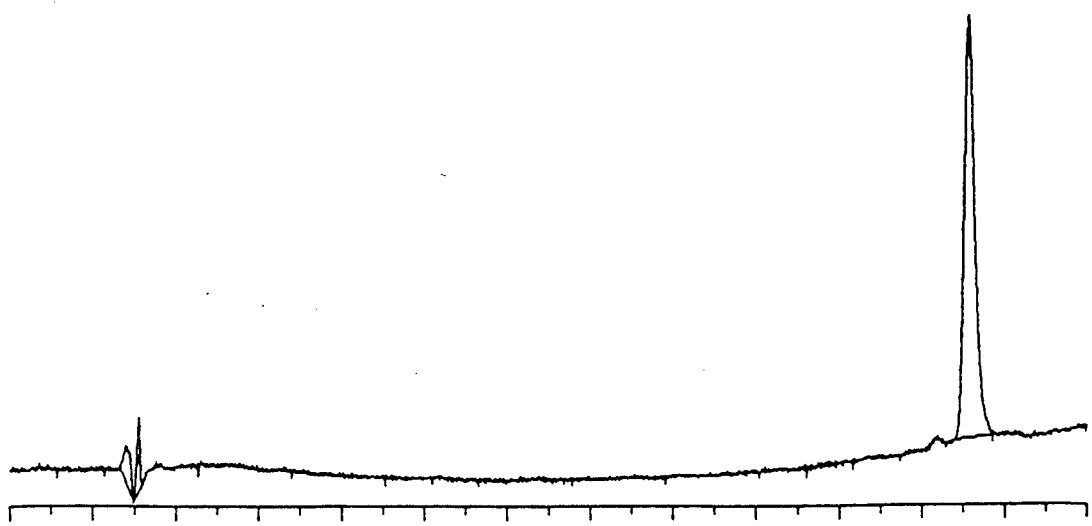

C-TERMINAL CAT FUSION PROTEIN AND PROCESS OF PREPARATION BY RECOMBINANT DNA

This is a continuation of application Ser. No. 06/690,488, filed as PCT/GB84/00179, May 24, 1984, which was abandoned upon the filing hereof.

This invention relates to a process for the production of a fusion protein comprising an active portion of a chloramphenicol acetyltransferase (CAT) protein and a polypeptide, the fusion protein per se, a process for the production of the polypeptide, a gene coding for the fusion protein, a vector including the gene, a host organism transformed with the vector and a process for raising antibody.

Recombinant DNA techniques of genetic manipulation allow for the insertion of a foreign gene into a host organism. The cells of the host organism may then produce the protein or polypeptide for which the foreign gene codes. Such modified, or transformed, host organisms provide a reproducible culture source for the large scale production of polypeptides or proteins using industrial fermentation techniques.

Many of the products to which recombinant DNA techniques have been applied are polypeptides such as human or animal hormones. It has been found that when the polypeptide is of relatively small size only low concentrations of the polypeptide product accumulate in the host cells. Such low accumulations of product, coupled with the necessary time consuming and expensive processes of purification render commercial working uneconomic. It appears that this low accumulation of product may be due, at least in part, to proteolytic turnover of the foreign product by the host cells.

In order to increase the yield of foreign products, such products have been produced as fusion products in which the polypeptide product is fused to a larger protein which is known to accumulate in the host organism. This may be achieved by ligating a gene coding for a protein known to be produced abundantly in the selected host organism, with a gene coding for the desired product, in the correct reading frame and without intervening stop codons. Examples of such abundantly produced protein are anthranylate synthetase (Trp gene product) and β-galactosidase (lacZ gene product). Published European patent application EP-A2-0001930 (Genentech Inc.) describes the production of a fusion protein comprising β-galactosidase and somatostatin, and a fusion protein comprising β-galactosidase and either the A or B chain of human insulin. Such fusion proteins must be cleaved to recover the desired polypeptide. The fusion proteins were cleaved using cyanogen bromide which selectively attacks methionine residues in a protein. Fortuitously, the desired products do not contain any methionine residues and are therefore unaffected by the cleavage procedure. In general, the procedures used for recovery and purification of such fusion proteins are complex and costly. In addition, the production of heterologous polypeptides or proteins by a host organism strains the cell metabolism and high level production causes instability of the cell line. The proteins referred to above, which are used to form a fusion protein with desired polypeptides, are large in comparison with a typical polypeptide product. The desired polypeptide therefore represents only a small percentage of the fusion protein produced by a transformed host organism, the efficiency of the process is low and the cost is high.

Fusion proteins comprising CAT and procaryotic proteins are known. These fusion proteins have resulted from a deletion mutation in bacterial plasmids (Iida et al The EMBO Journal 1 No. 6 p 755–759 (1982), spontaneous chloramphenicol resistant revertants (Betz, J. L. et al Gene 15 p 187–200 (1981)) and accidental deletion of stop codons (Goldfarb, D. S. et al in "Molecular Cloning and Gene Regulation in Bacilli" Academic Press, Ed. Ganesan, A. T. et al (1982) p 311–324 and Close, T. J. et al Gene 20 p 305–316 (1982)).

The object of the invention is to provide a process for the production of a fusion protein capable of production at high levels in a host organism. A further object of the invention is to provide a fusion protein which may be readily isolated and purified, readily cleaved to yield a desired polypeptide, and which comprises a relatively small protein fused to a polypeptide. Further objects are to provide a gene coding for such a fusion protein, a vector including such a gene and a host organism transferred with such a vector.

According to a first aspect of the invention we provide a process for the production of a fusion protein comprising an active portion of a chloramphenicol acetyltransferase (CAT) protein and a eucaryotic polypeptide the process comprising culturing a host organism transformed with a vector including a gene coding for the fusion protein to obtain expression of the gene, and isolating the fusion protein.

According to a second aspect of the invention we provide a process for the production of a fusion protein comprising a heterologous polypeptide linked to the carboxy terminus of an active portion of a chloramphenicol acetyl transferase (CAT) protein, the process comprising culturing a host organism transformed with a vector including a gene coding for the fusion protein to obtain expression of the gene, and isolating the fusion protein.

As used herein the term "active" refers to the presence, in the CAT portion of the fusion protein, of a binding site for a CAT substrate. Preferably the CAT portion has catalytic activity as an acetyltransferase for a CAT substrate. The CAT portion preferably binds reversibly to a CAT substrate and may be removed therefrom under relatively mild conditions. The portion of the CAT protein may be the entire CAT protein, an active part thereof or an active analogue thereof.

As used herein the term "polypeptide" refers to a compound comprising two or more amino acid residues linked together in a linear chain by peptide bonds. The term includes proteins with a defined secondary structure (in the form of folding of the polypeptide chain) and polypeptide not exhibiting a defined secondary structure. Preferably however the term relates to polypeptides having a relatively short chain length.

As used herein the term "eucaryotic" polypeptide refers to a polypeptide found naturally in a eucaryote or to a derivative precursor, or analogue thereof. The eucaryote may be a simple organism such as a yeast or a complex organism such as an animal or plant.

The fusion protein produced by the process may be readily detected and assayed by detecting and measuring catalytic activity on a CAT substrate.

As used herein the term "heterologous" polypeptide refers to a polypeptide not indigenous to or normally accumulated in the host organism.

CAT is abundantly produced, readily detectable and is a relatively small protein. The production of a CAT fusion protein with a polypeptide therefore provides an advantageous polypeptide production route.

It has surprisingly been discovered that a CAT fusion protein produced by the above described method is susceptible to purification by CAT substrate affinity chromatography, previously known only for the purification of naturally-occurring CAT's (Zaidenzaig, Y and Shaw, W. V. FEBS Lett. 62 No. 3, p 266-271, (1976)). This is particularly unexpected in the case of a carboxy fusion because the chloramphenicol binding domain is located close to the carboxy terminus of the CAT primary sequence. Preferably the fusion protein is isolated by affinity chromatography using a solid phase to which is bound a substrate to which the active portion of the CAT protein is capable of specifically binding.

This type of substrate affinity chromatography is highly specific because it depends upon the selective interaction between an enzyme and its substrate and thus advantageously ensures highly purified product.

In the isolation or purification step, the CAT fusion protein bonds with CAT substrate immobilised on a solid phase and permits purification.

The active portion of CAT protein may be derived from any procaryotic protein (see Shaw, W. V. CRC Crit. Rev. Biochem. 14 p 1-46 (1983)). Examples of such CAT proteins are the enterobacterial CAT variants (for example types I, II, III) and staphylococcal variants (for example types A, B, C, D) which are known in the art. These proteins may be used complete, or may be shortened, provided that they retain the active site necessary for binding to a CAT substrate.

The CAT substrate may comprise any ligand to which the active portion of the CAT protein forming part of the fusion protein is capable of selectively binding. This ligand may comprise chloramphenicol or an analogue such as 'chloramphenicol base' (see Zaidenzaig, Y and Shaw, W. V.). The ligand may comprise acetyl-CoA or an analogue of this compound which is bound by CAT. In addition certain variants of CAT, for example the type I CAT variant, recognise and bind to the antibiotic fusidic acid, and analogues thereof (see Bennett, A. D. and Shaw, W. V. Biochem. J., (1983) Biochem. J. 215 p 29-38 (1983)) as well as certain triphenylmethane dyes (Proctor and Rownd, J. Bacteriol, 150 p 1375-1382, (1982) and such compounds may be used as ligands for affinity purification of the CAT fusion protein. The immobilised CAT substrate may therefore comprise any suitable CAT binding ligand or appropriate combinations thereof. The CAT substrate may be bound to any suitable inert solid phase either irreversibly or via a linkage susceptible to chemical or enzymic cleavage, (for example a disulphide bond).

Any appropriate CAT substrate affinity chromatography procedure may be used for the purification of the CAT fusion product. Preferably, crude transformed host cell products, containing the fusion protein, are contacted with an immobilised CAT substrate which may be, for example, in the form of a column, to which the fusion protein selectively binds. The other components of the crude transformed host cell products may be separated from the bound fusion protein by washing treatment. For instance, the solid phase comprising bound fusion protein may be washed with a wash buffer and the other components eluted therefrom. The wash buffer used preferably provides an environment in which fusion protein binding is substantially maintained.

Subsequent to washing, the bound fusion protein may be recovered, usually by appropriate elution treatment, in which the solid phase is treated with an elution buffer which frees fusion protein from the immobilised substrate. The elution treatment may involve a variation of one or more components such as pH, ionic strength, temperature, or other treatment (e.g. with an organic solvent or redox reagent) which alters the binding state of the fusion protein and promotes its release from the substrate. Preferably however the elution treatment comprises treatment with a solution of a CAT substrate. The substrate for elution, may comprise any of those ligands which may be used as CAT substrates, including chloramphenicol, acetyl-CoA, fusidic acid, triphenylmethane dyes or analogues of any of these, either singly or in appropriate combination. A particularly preferred elution buffer comprises a solution of chloramphenicol, for example, a solution containing 0.6M sodium chloride, 5 mM chloramphenicol.

Preferably the host organism is a bacterium and the culture medium includes chloramphenicol or a bacteriocidal analogue thereof capable of inactivation by a CAT protein.

The production of a fusion protein having CAT activity advantageously provides simultaneous protein production and a useful selection marker. Transformed bacteria frequently reject vectors which include foreign genetic material. The fusion protein produced by the process of the invention itself has chloramphenicol transferase activity. Its production therefore confers on a transformed bacteria, resistance to chloramphenicol. The transformed bacterium may thus be grown in a culture medium supplemented with chloramphenicol, resulting in a selection of those bacterial cells which have retained the vector including the gene coding for the fusion protein. In addition recombinant DNA vectors frequently undergo spontaneous rearrangement which may result in the destruction of a selective marker. The close proximity in the fusion protein of CAT and the polypeptide reduces to a minimum the risk of such a rearrangement affecting the percentage of transformed cells carrying the desired product gene.

According to a third aspect of the invention we provide a fusion protein comprising an active portion of a chloramphenicol acetyltransferase (CAT) protein and a eucaryotic polypeptide. The fusion protein may be produced by the process of the first aspect of the invention.

The eucaryotic polypeptide may be fused into the CAT protein, onto the amino terminus of the CAT protein, or onto the carboxy terminus of the CAT protein. For instance, an internal fusion may be produced by insertion of the gene coding for the eucaryotic polypeptide into a restriction site, such as the EcoRI site of the type I CAT variant gene (see Betz, J. L. and Sadler, J. R. Gene 15 p 187-200 (1981) within the DNA sequence coding for the CAT protein.

Preferably however the polypeptide is linked to the carboxy terminus of the chloramphenicol transferase protein. This type of fusion protein has a number of advantages. Firstly, the natural CAT promoter and/or its ribosome binding site may be used for the expression of the fusion protein either alone or in combination with an additional promoter or ribosome binding site. An N-terminal fusion would require the removal of a methionine residue from the amino terminus of the eucaryotic peptide. An internal fusion would require cleavage at both ends of the eucaryotic polypeptide rendering the overall process more complex.

According to a fourth aspect of the invention we provide a fusion protein comprising a heterologous polypeptide linked to the carboxy terminus of an active portion of a chloramphenicol acetyltransferase (CAT) protein.

Preferably the eucaryotic or heterologous polypeptide is linked to the active portion of the CAT protein through a linkage capable of selective chemical or enzymic cleavage.

As used herein the term "selective" cleavage refers to a cleavage which may be carried out without substantially affecting the eucaryotic or heterologous polypeptide. Such linkages may be provided conveniently at the DNA level by incorporation of appropriate DNA sequences at, or adjacent to, the end(s) of the DNA sequence coding for the polypeptide in the DNA sequence which codes for the fusion protein.

Two specific such linkages are however preferred. The first preferred linkage is a glutamic acid amino acid residue diradical. The inclusion of a glutamic acid residue between the eucaryotic or heterologous polypeptide and the active portion of CAT protein allows for the cleavage of the fusion protein to release the eucaryotic or heterologous polypeptide. The fusion protein may be cleaved at the glutamic acid residue site using an acid protease from Sorghum (E.C.3.4.23.14-Garg, G. K. et al Eur. J. Biochem. 17 No. 4 (1970), a sea urchin hatching protease (E.C.3.4.24.12-Lopez, G. W. et al Biol. Bull. 147 p 489 (1974) or preferably staphylococcal protease (E.C.3.4.21.19).

Alternatively, the linkage may be a lysinearginine peptide diradical. Cleavage at this site may be achieved using a mouse sub-maxillany gland protease or preferably clostripain (E.C.3.4.22.8.).

A further example of such a linkage is a four amino acid residue blood coagulation factor $X_a$ site (ileuglugly-arg$\pm$x) (E.C.3.4.21.6.).

The eucaryotic polypeptide may be a protein such as a human or animal immunoglobulin, albumin, enzyme (e.g. chymosin), enzyme precursor (e.g. prochymosin, preprochymosin) or a derivative or analogue thereof. Preferably however the polypeptide is a relatively small human or animal polypeptide. Such polypeptides include hormones such as insulins, adrenocorticotrophic hormone (ACTH), growth hormones, calcitonins and precursors and derivatives thereof, for example calcitonin-glycine. The products may also comprise antigenic peptides, for example a foot and mouth disease virus (FMVD) antigenic polypeptide.

Preferably however the polypeptide is a calcitonin or a derivative thereof. Most preferably the polypeptide is calcitonin-glycine. Particulary preferred fusion proteins comprise an active portion of a CAT protein, a linkage of the type described above and either calcitonin or calcitonin-glycine.

In a fifth aspect of the invention we provide a process for the production of a polypeptide comprising the steps of producing a fusion protein comprising an active portion of a chloramphenicol acetyltransferase (CAT) protein and a polypeptide by culturing a host organism transformed with a vector including a gene coding for the fusion protein to obtain expression of the gene, cleaving the fusion protein and isolating the polypeptide. Preferably we provide a process for the production of a polypeptide comprising the steps of preparing a fusion protein according to the third or fourth aspect of the invention by a process according to the first or second aspect of the invention, cleaving the fusion protein, and isolating the polypeptide.

Preferably we provide a process in which, after cleavage of the fusion protein in solution, the pH of the solution is adjusted to a level effective to cause precipitation of the active portion of the chloramphenicol acetyltransferase protein, leaving the polypeptide in solution, and the polypeptide is isolated. The CAT protein is insoluble in acid solution and therefore if the polypeptide to be produced is soluble, precipitation of the CAT protein by a reduction in pH provides an advantageous method for heterogeneously separating the unwanted CAT protein from the desired polypeptide.

Preferably, where the fusion protein comprises a glutamic acid residue linkage, cleavage of the fusion protein is carried out with staphylococcal protease. Preferably, where the fusion protein comprises a lysinearginine linkage the cleavage is carried out with clostripain.

The cleavage step may be carried out upon the fusion protein attached to an affinity matrix, such as an affinity column used for purification of the fusion protein.

Natural calcitonin may be produced from calcitoninglycine by enzymic conversion to produce a natural, amidated proline at the carboxy terminus of the polypeptide. Alternatively, where the polypeptide has the amino acid sequence of calcitonin (but no amidation of the terminal proline), an analogue of natural calcitonin (with a carboxy terminal amidated proline) may be produced by amidation. Such amidation results in amidation of amino acid 15, changing aspartic acid to asparagine.

In a sixth aspect of the invention we provide a gene coding for a fusion protein according to the third or fourth aspect of the invention.

In a seventh aspect of the invention we provide a vector including a gene according to the sixth aspect of the invention.

Expression vectors containing recombinant DNA coding for the CAT fusion protein may be constructed, host cells transformed with these vectors and fusion protein products expressed by the transformed host cells using procedures well known in the field of recombinant DNA technology. The vector may be a plasmid or virus capable of maintenance in a transformed host organism, episomally or chromosomally. Typically the recombinant DNA is prepared by a restriction enzyme cleavage of the DNA coding for the CAT protein followed by ligation with a heterologous gene coding for the eucaryotic polypeptide. The heterologous gene may be attached at or near the 3' or 5' end of, or inserted within, the CAT protein DNA sequence. Attachment of the heterologous gene at or near the 3' end of the CAT protein DNA is preferred and results in a carboxy terminal fusion. To facilitate construction of the requisite recombinant DNA sequence it may be necessary to introduce an appropriate restriction enzyme cleavage site in the CAT protein DNA sequence. Preferably the fusion protein lies downstream of a strong inducible promoter such as a trp promoter.

According to an eighth aspect of the invention we provide a host organism transformed with a vector according to the seventh aspect of the invention. The host organism may be selected from a bacterial host organism or a eucaryotic host organism such as a yeast or mammalian cell.

According to a ninth aspect of the invention we provide a process for raising antibodies to a polypeptide comprising immunising an animal with a fusion protein according to the third or fourth aspect of the invention.

It is known that certain polypeptides (in particular small polypeptides) do not produce a satisfactory immune response when used as an immunogen for raising antibodies. Previously such small polypeptides have been chemically bound to large structures such as ovalbumin for use in an immunogen. We have discovered that a fusion protein of the third or fourth aspect of this invention acts as an effective immunogen for the raising of antibodies. The antibodies so produced may be harvested from the immunised animal directly or the immune response may be utilised in the formation of monoclonal antibody. The process of this aspect of the invention may be used for the production of vaccine where the polypeptide is a polypeptide including an epitope of the antigen to which antibodies are required.

Embodiments of the invention are now described in the following Examples which refer to the accompanying drawings, in which:

FIG. 1—shows the 5' terminal nucleotide sequences of the genes coding for native CAT and for the described carboxy terminal fusion proteins, FIG. 2—shows schematically the construction of the plasmids described, FIG. 3—shows an SDS polyacrylamide gel of the products of some of the plasmids described. (The lanes of the gel are as follows:

Lane 1—*E. coli* HB101 whole cells:

Lane 2—*E. coli* HB101 soluble fraction:

Lane 3—*E. coli* HB101 insoluble fraction:

Lane 4—substrate affinity purified native $CAT_I$ from *E. coli* C600 containing pBR 328:

Lane 5—*E. coli* HB101 whole cells containing plasmid pAB 74:

Lane 6—as Lane 5-soluble fraction:

Lane 7—as Lane 5-insoluble fraction:

Lane 8—*E. coli* HB101 whole cells containing plasmid pCT 2024:

Lane 9—as Lane 8-soluble fraction:

Lane 10—as Lane 8-insoluble fraction:

Lane 11—$CAT_I$-lys-arg-hCT-glycine-purified from insoluble fraction of Lane 10:

Lane 12—*E. coli* HB101 whole cells containing plasmid pCT 2026:

Lane 13—as Lane 12-soluble fraction:

Lane 14—as Lane 12-insoluble fraction:

Lane 15—$CAT_I$-glu-hCT-glycine purified by substitute chromatography from soluble material)

Figure 4:
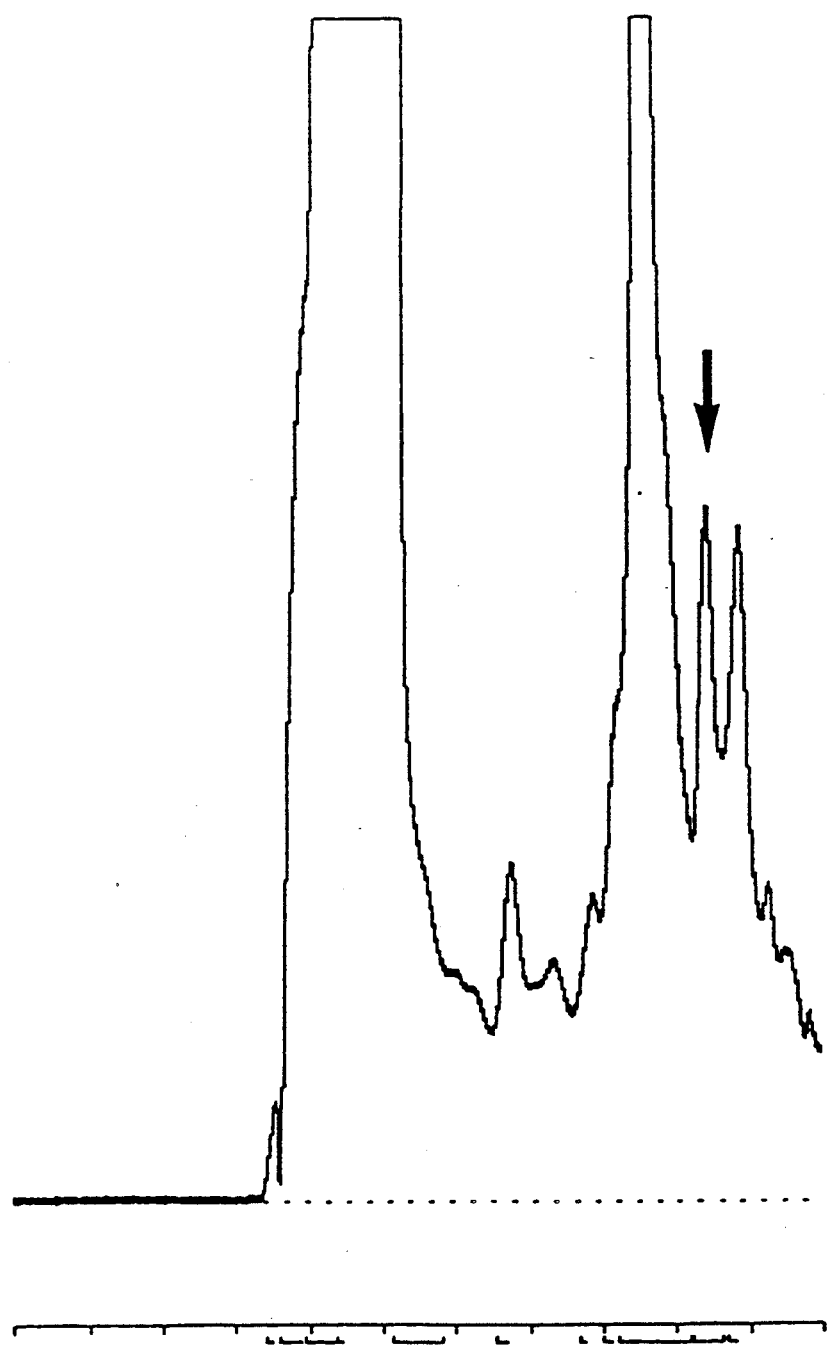
Figure 5:
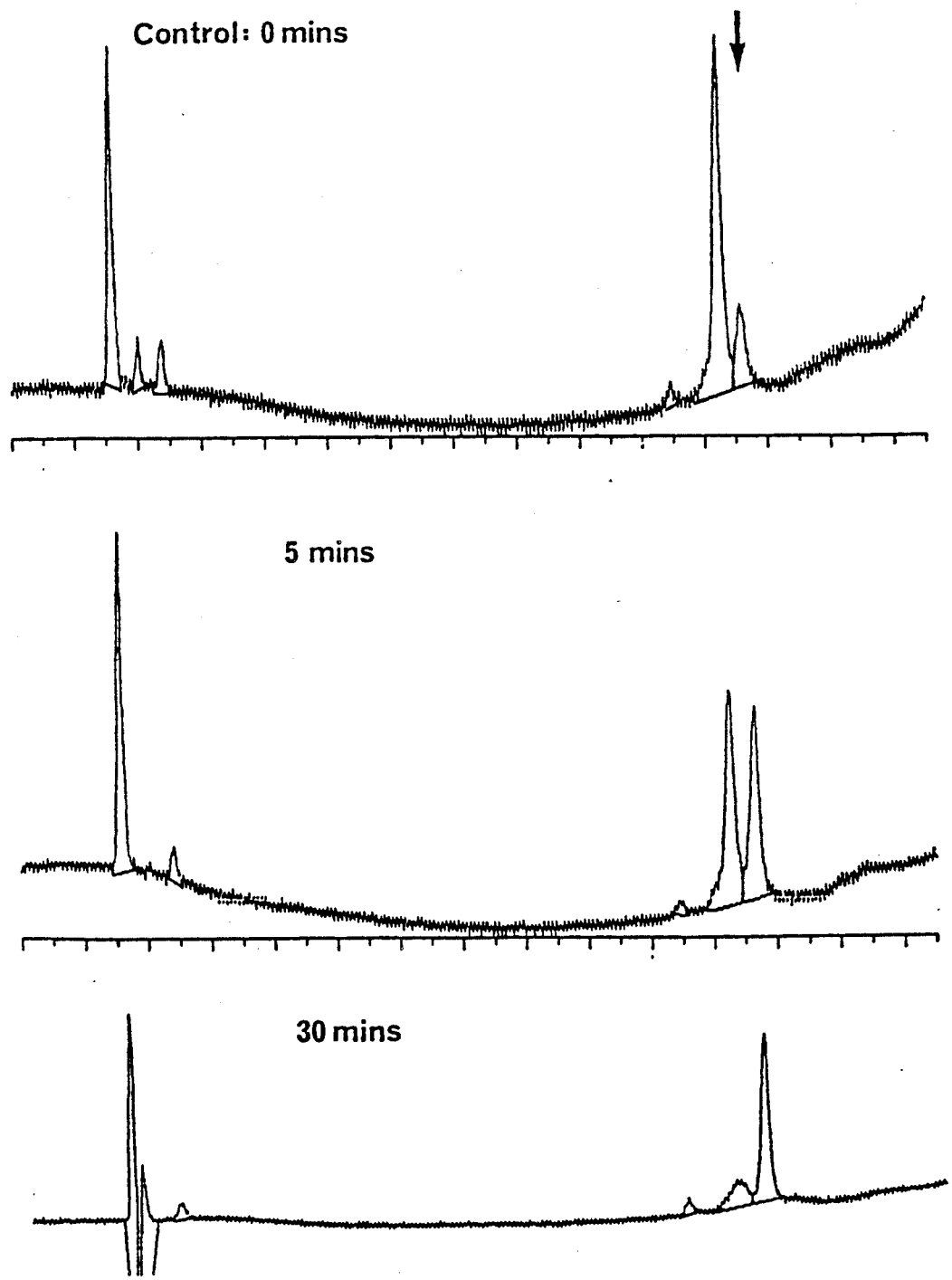
Figure 7:
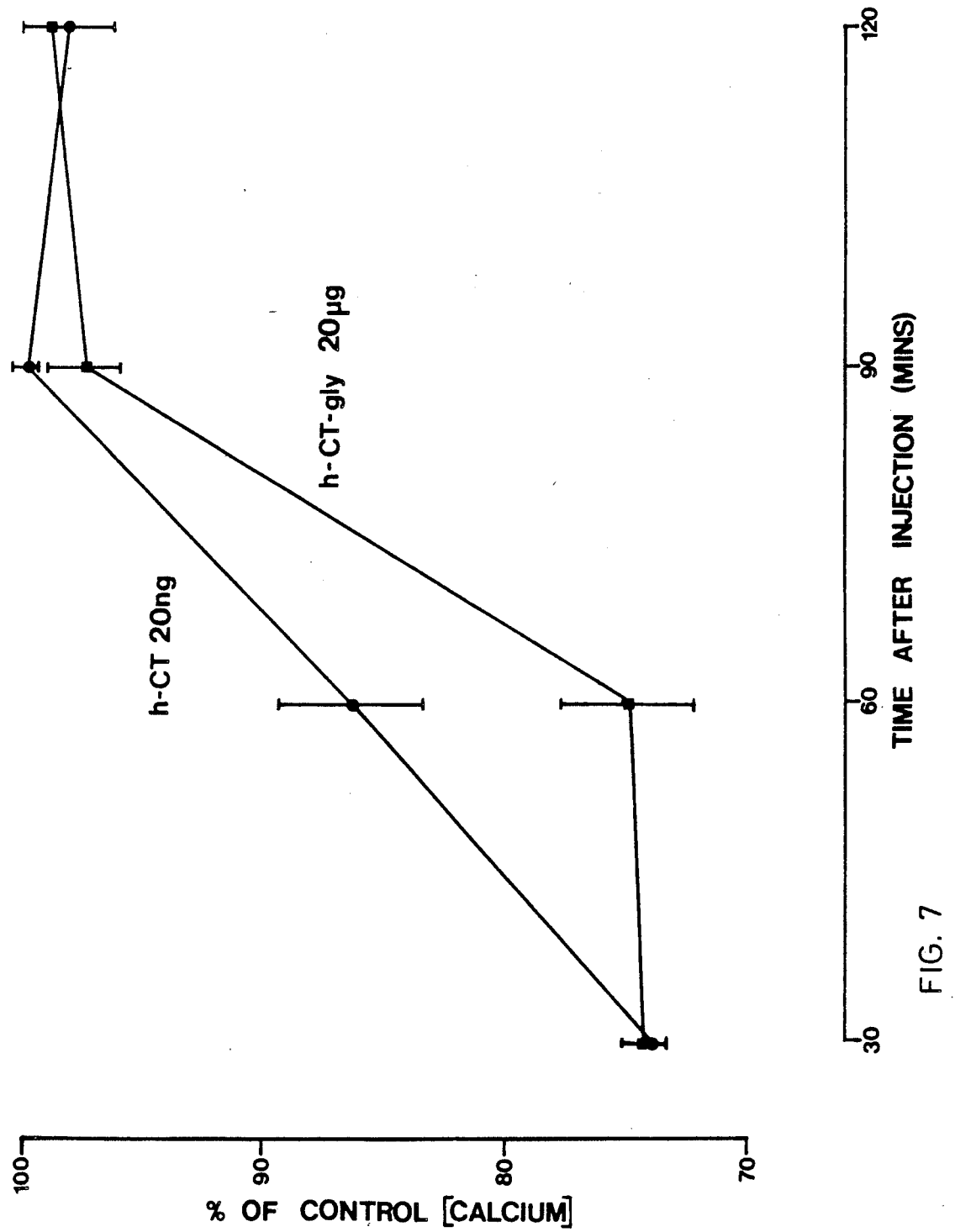

FIG. 4—shows the result of HPLC carried out on the human calcitonin-glycine produced by cleaving the fusion protein expressed by plasmid pCT 2024, FIG. 5—shows successive HPLC results monitoring the formation of a 1,7 disulphide bond in human calcitonin-glycine by air oxication, FIG. 6—shows a comparison between the HPLC results obtianed with chemically synthesised human calcitonin (A) and human calcitonin-glycine produced by the process of the invention (B), FIG. 7—shows a comparison of the bioactivity (measured as a lowering of serum calcium concentration in rats) between authentic human calcitonin (h-CT) and human calcitonin-glycine (h-CT-gly).

GENERAL

It was decided to construct fusion protein vector plasmids capable of transforming host cells to express fusion proteins in which the foreign polypeptide or protein is fused onto the carboxy terminal of a type I CAT protein. In the CAT substrate affinity chromatography purification procedure hereinafter described, it is required that the fusion protein recognises and binds to a close structural analogue of chloramphenicol, e.g. 'chloramphenicol base'. Thus the fusion protein must contain a substantial proportion of the native CAT protein so that it can adopt the correct conformation to recognise and bind to the immobilised substrate.

A carboxy terminal fusion of the type I variant was chosen since it is known that the type I enzyme is expressed at high level in the chosen host organism, *E. coli* (Bennett A. D. and Shaw W. V., Biochem J 215, 29–38, 1983), and thus such a fusion might be expected not to disrupt the 5' end of the structural gene which is critical for high level expression. Additionally the use of such a fusion would obviate the need to remove a formyl methionine amino acid residue from the amino terminal of the foreign polypeptide or protein product, a problem which would be encountered with amino terminal fusions.

The chloramphenicol acetyltransferase type I ($CAT_I$) gene, however, contained no suitable restriction sites in the 3' coding region which would permit the construction of such a fusion (FIG. 1). (NB. This situation has now changed due to the commercial availability of the restriction enzyme Sca1).

Accordingly a family of $CAT_I$ fusion vector plasmids were constructed that encoded a substantial proportion of the native enzyme and which carried useful restriction sites in the desired region of the $CAT_I$ gene.

$CAT_I$ fusion proteins which are amenable to substrate affinity chromatography are, in general, preferred. Recognition of the immobilised affinity substrate is closely allied to catalytic activity. The most suitable fusion vector plasmids are thus likely to be those which encode proteins which will acetylate chloramphenicol. Since chloramphenicol is an antibiotic, and since acetylation inactivates the antibiotic, the fusion vector plasmids which are most likely to be of practical use are those which retain the ability to confer chloramphenicol resistance to *E. coli*.

It was therefore, decided to use chloramphenicol resistance as the basis for a selection procedure for a family of $CAT_I$ fusion vector plasmids. This selection could best be used, however, if the starting gene was substantially intact and yet the protein which it encoded was defective with regard to chloramphenicol resistance.

Such a suitable plasmid had previously been isolated by Pst1 digestion of the DNA of a weakly chloramphenicol resistant R100 R-plasmid mutant and subsequent ligation of a single Pst1 fragment into the Pst1 site of plasmid pBR322 (Iida et al (1982) EMBO J 1, 755–759). The plasmid, pBR322: Cm104 was obtained and encodes a $CAT_I$ enzyme that has had the last seven amino acid residues of the carboxy terminus removed by deletion. The removal was due to a spontaneous in vivo mutation which involved the insertion element IS1. However, the resulting DNA molecule has no termination codon at the end of the $CAT_I$ structured gene. The ribosome, therefore, translates into protein the RNA transcribed from the IS1 DNA until it meets an in phase termination codon. The net result is a CAT$_I$ protein nineteen amino acid residues longer than the native enzyme in which the last twenty-six amino acid residues are directed by the IS1 DNA sequence (FIG. 1).

This mutant structural gene also lacks any suitable restriction sites which would be useful to create a desirable fusion protein so a series of DNA manipulations were performed.

EXAMPLE 1

Construction of a Family of CAT$_I$ Fusion Vector Plasmids

A) Fusion Vector Plasmid Constructions

DNA manipulations were performed essentially as described by Maniatis et al (Molecular Cloning, Cold Spring Harbor, N.Y., 1982), with minor modifications. The DNA sequence of the 3' terminus of the CAT$_I$ genes of all of the plasmid constructs described, with the exception of the CAT$_I$ met-prochymosin construct, were determined by one of either of the two methods which are well known in the art, i.e. the Maxam and Gilbert or M13 dideoxy DNA sequencing methods.

A Pst1 restriction fragment containing the mutant CAT$_I$ gene outlined above was isolated from plasmid pBR322: Cm104 and ligated into the dephosphorylated Pst1 site of plasmid pAT153. The plasmid pAT/Cm104b (FIG. 2) was chosen since in this orientation both the CAT$_I$ and β-lactamase promoters transcribe in the same direction. This cloning maneouvre was primarily to construct a plasmid which carries a unique Tth111I restriction site. This cleavage site is derived from the IS1 DNA which was joined to the end of the CAT$_I$ structural gene and lies in the nineteenth amino acid codon of the twenty-six amino acid residue extension (FIG. 1).

Plasmid pAT/Cm104b was linearised with Tth111I and digested with BAL31 exonuclease. Samples at a series of time points were withdrawn and the reaction was stopped using excess EDTA. Any non-flush ends created by the BAL31 digestion were filled in using the Klenow fragment of DNA polymerase I. These plasmid DNA molecules were then dephosphorylated using calf intestinal phosphates. Next a kinased linker, R140 with the sequence

5'-TCAGATCTGGAGCTCCAGATCTGA-3' was ligated to each plasmid time point sample. After ligation the plasmid DNAs were digested with SstI restriction endonuclease and re-ligated to ensure that only one linker was present in each plasmid.

These sets of DNA molecules were then transformed into E. coli DH1 and fusion vector plasmids were selected on the basis of vigorous growth on L-agar containing 20 μg/ml chloramphenicol.

Small scale plasmid preparations were performed. A number of plasmids which carried a single Sst1 restriction site (derived from the linker DNA) and which also generated a comparatively small DNA fragment when simultaneously digested with EcoR1 and BglII were isolated. DNA sequence analysis revealed that in plasmid pAB7, pAB8 and pAB19 the linker DNA had been attached to the 3' end of the CAT$_I$ structural gene in each of the three reading frames (FIGS. 1 and 2).

Plasmid pAB19 was digested with BglII and dephosphorylated. To this was ligated a Sau3A1 restriction fragment encoding lysine-arginine-calcitonin-glycine. This fragment was derived from a cDNA clone isolated by Roger Craig (Nature 295, 345-347, 1982) and was isolated from a trpE protein lysine-arginine-calcitonin-glycine fusion plasmid (from plasmid pE2; WO 84/00380). Plasmid pAB19 was selected since it contained the BglII site in the correct reading frame for in phase fusion to CAT$_I$. The ligation mix was transformed into E. coli DH1 and tetracycline resistant colonies were selected. Small scale plasmid preparations were made from these colonies and screened for the presence of the calcitonin gene-derived Sph1 restriction site in the correct orientation with respect to the EcoR1 site in the CAT$_I$ gene.

A plasmid, pAB74, was isolated and Western blot analysis confirmed the presence of a protein which was slightly larger than CAT$_I$ and immunoreactive with rabbit antisera raised against ovalbumin-conjugated authentic human calcitonin (data not shown). DNA sequence analysis, however, demonstrated that in vivo recombination had occurred due to the presence of a common nine nucleotide sequence found in both the IS1 DNA and in the calcitonin cDNA thus deleting the lysine-arginine enzymic cleavage site (FIGS. 1 and 2).

Preliminary experiments were performed to investigate the level of CAT$_I$ fusion protein expressed from plasmid pAB74. These experiments indicated a moderately high level of synthesis (FIG. 3). However, expression from the CAT$_I$ promoter is constitutively regulated and hence could be expected to have an adverse effect on cell growth.

Therefore, in order to achieve higher levels of CAT$_I$ fusion protein synthesis and to still maintain a short cell doubling time it was decided to put all three fusion vector genes under the control of the strong, inducible, tryptophan biosynthesis (trp) promoter.

Plasmids pAB7, pAB8 and pAB19 were each digested with restriction enzyme SstI and incubated with S1 exonuclease. After phenol/chloroform extraction and ethanol precipitation these blunt-ended plasmid molecules were digested TaqI and DNA fragments of approximately 750 base pairs were isolated. These fragments contain the entire CAT$_I$ fusion structural genes with BglII sites in three reading frames but lack the CAT$_I$ promoter (FIG. 2).

These CAT$_I$ genes were then put under the control of the trp promoter of plasmid pCT54 (Emtage et al, Proc Natl Acad Sci USA 80, 3671-3675, 1983). This plasmid also has the advantage of having a transcription terminator sequence so that high level expression is limited to the gene cloned upstream of this sequence and downstream of the trp promoter. Plasmid pCT54 was digested with EcoR1 and the 5' cohesive ends were filled in using the Klenow fragment of DNA polymerase I. Subsequent restrictions of this molecule with the enzyme ClaI followed by dephosphorylation created a molecule which would accept the CAT$_I$ fusion vector gene cartridges isolated above. Ligation of this molecule with a 3-fold molar excess of each the CAT$_I$ gene cartridges followed by transformation of E. coli HB101 gave the chloramphenicol resistant fusion vector plasmids pCT201, pCT202 and pCT203 (FIGS. 1 and 2). (NB in all three cases the manipulation result in the reformation of the EcoR1 site of pCT54).

B) Construction of CAT$_I$-Calcitonin Glycine Fusion Protein Plasmids

One of the above constructs pCT202, was subsequently used as the basis for two plasmids which inducibly express CAT-human calcitonin-glycine fusion proteins at high levels.

The fusion vector plasmid pCT202 was selected since the CAT gene of this plasmid has its unique BglII site in the correct reading frame for fusion to a gene for lysine-arginine-calcitonin-glycine carried on a BglII-PstI fragment and which was isolated from the plasmid pE2 mentioned above. Ligation of this fragment with BglII-PstI digested pCT202 gave the chloramphenicol resistance-conferring plasmid pCT2024 (FIGS. 1 and 2).

The fusion protein is produced in large amounts by $E.$ $coli$ (FIG. 3). However, initial results from Western blot analyses (data not shown) indicated that the bacteria partially processes the fusion protein in vivo. Additionally experiments indicated that the desired fusion protein was found in the insoluble fraction. Furthermore during extraction (see Example 2 below) of this insoluble material the bacterial proteases cause a further and extensive cleavage of the fusion protein in vitro. Experiments on the fusion protein synthesised by plasmid pAB74 which lacks the proteolytic cleavage site, indicated that this protein was both soluble and non-proteolysed (FIG. 3). This implied that neither insolubility nor susceptibility to proteolysis was due to the calcitonin polypeptide moiety per se. At this point it was decided to investigate the use of staphyloccocal protease as the fusion protein cleavage enzyme. Staphyloccocal protease cleaves after acidic residues but this specificity can be decreased to glutamic acid under defined buffering conditions. Preliminary experiments indicated that under appropriate conditions this protease had very low activity against authentic, chemically synthesised, human calcitonin since the polypeptide contains no glutamic acid residues (data not shown). In addition, conversion of the lysine-arginine cleavage site to a glutamic acid residue was envisaged to restore the charge distribution at the carboxy terminus of $CAT_I$-calcitonin protein to a distribution that was closer to that of native $CAT_I$. This it was hoped might restore solubility.

Plasmid pCT2024 was digested with NarI and the largest fragment isolated and re-circularised by ligation (FIG. 2). A plasmid pCT2024 Nar was isolated that was then doubly digested with BglII and SphI restriction enzymes at sites, which are each unique in this plasmid (FIG. 2). The plasmid molecule produced was then ligated with an excess of the following oligonucleotides:

| R232 | 5'- GATCTGAATGTGGCAA -3' |
| R233 | 5'- CAAGTAGACAGGTTGCCACATTCA -3' |
| R234 | 5'- CCTGTCTACTTGCATG -3' |

Of the three oligonucleotides only the latter two, R233 and R234 were kinased prior to the ligation reaction. The resultant plasmid molecules were transformed into $E.$ $coli$ HB101 cells and the desired transformed cells selected by growth on media containing ampicillin (100 μg/ml). Transformation and selection was followed by small scale plasmid preparations from the resulting ampicillin resistant colonies and digestion of these DNA samples with the restriction enzyme AccI. A Plasmid containing an AccI site, pCT2026, was isolated and shown to confer chloramphenicol resistance (FIGS. 1 and 2). Plasmid pCT2026 directs the high level inducible expression of the soluble $CAT_I$ fusion protein, $CAT_I$-glutamic acid-calcitonin-glycine and is far less susceptible to proteolysis than $CAT_I$-lysine-arginine-calcitonin-glycine (FIG. 3). (NB In making this construct the nine nucleotide repeat sequence which was involved in the in vivo formation of pAB74 was altered by appropriate codon selection. This was possible because of the redundancy of the genetic code. The alteration, it was hoped, would reduce the likelihood of any potential subsequent in vivo re-arrangement of the plasmid).

EXAMPLE 2

Preparation and Cleavage of Cat-Calcitonin Fusion Proteins

As described in Example 1 plasmids pCT2024 and pCT2026 have been constructed which code for expression of $CAT_I$-Lys-Arg-human calcitonin (hCT)-Gly and $CAT_I$-Glu-hCT-Gly respectively. These plasmids have been transformed into $E.$ $coli$ HB101 cells and the fusion proteins have been expressed at high level by the transformed cells. The methods used for recovery and cleavage of these fusion proteins and subsequent purification of the hCT-Gly product were as follows:

1) $CAT_I$-Lys-Arg-hCT-Gly

A) Preparation of insoluble $CAT_I$-Lys-Arg-hCT-Gly Fusion Protein $E.$ $coli$ HB101 cells containing plasmid pCT2024 were cultured at 37° C. to the late exponential phase of growth in a 10 liter fermenter in supplemented mineral salts medium containing 20 μg/ml chloramphenicol. The cells were harvested by centrifugation (1,000 rpm × 10 minutes). The cells (22 g wet weight) were resuspended in 60 ml of 50 mM Tris-HCl buffer, pH 8.0, containing 100 mM NaCl and 1 mM EDTA. 0.2 ml of PMSF solution (8.3 mg/ml in ethanol) and 21.4 mg of lysozyme were then added to the suspension. After 25 minutes 2 ml of 4% (w/v) deoxycholate solution was added and the resultant viscous suspension was left to stand for a further 10 minutes. 0.6 mg of DNase 1 was added and the suspension was left to stand for up to a further 30 minutes at room temperature until the viscosity had decreased markedly. At completion of this stage the suspension was centrifuged (11,000 rpm × 5 minutes, and the supernatant discarded. The pellets, which comprised the insolbule CAT-Lys-Arg-hCT-Gly product, were washed with nine volumes of cold, buffered Triton X100 solution (50 mM Tris-HCl, pH 8.0, 10 mM EDTA, 0.5% (v/v) Triton X100, 100 mM NaCl) and recovered by centrifugation (11,000 rpm × 5 minutes). This wash procedure was then repeated twice. The pellets were collected and resuspended in 20 ml of the pH 8.0 Tris-HCl suspension buffer as described above. The fusion protein was checked for purity by SDS polyacrylamide gel electrophoresis (FIG. 3) and then the remaining suspension was aliquoted into 1 ml fractions and stored at −20° C.

B) Cleavage of $CAT_I$-Lys-Arg-hCT-Gly

Five 1 ml fractions as prepared above, containing a total of 44 mg of fusion protein, were thawed and centrifuged (15,000 g × 1 minute, Eppendorf tubes). The pellets obtained on centrifugation were then resuspended in 2 ml of a 0.1M Tris-HCl buffered 7.5M urea solution, pH 8.0 containing 0.14M 2-mercaptoethanol and the resultant fusion protein solution was then incubated at 37° C. for 5–10 minutes. 1.5 ml of distilled water was then added to the solution and digestion was started by addition of 0.41 ml of a solution which contained 1 mg of DTT activated/PMSF treated Clostripain (Sigma Product Number CO888). After 10-15 minutes digestion at 37° C., the reaction was stopped by addition of trifluoroacetic acid (1.3 ml, 20% v/v). The acidified solutions were left on ice for 10-20 minutes, and centrifuged (15,000 g×15 minutes, Eppendorf tubes) to remove the white protein precipitate which formed. Clostripain treatment cleaves the fusion protein and the acidified supernatant contains hCT-Gly peptide in solution.

C) Purification of hCT-Gly

Two 2.5 ml fractions of the acidified supernatant prepared above were loaded onto a semi-preparative reverse phase HPLC column (Synchropak RP-P, 25 cm×1.0 cm) and eluted, using a 30% to 45% acetonitrile: 0.1% (v/v) TFA in water gradient, over 20 minutes (2 ml/minute, 225 nm detection). Radioimmunoassay experiments with anti-authentic human calcitonin antiserum showed two immunoreactive peaks with retention times of 17.01 and 18.83 minutes (FIG. 4). The peaks were pooled and freeze dried. The white solid obtained was then dissolved in 2 ml of 50 mM Tris/HCl, pH 8.5 containing 2 mM EDTA and the resultant solution left to air oxidise at room temperature for 30 minutes. During this period the formation of the 1, 7 disulphide bond of the hCT-Gly was monitored by a similar reverse phase analytical HPLC column (10-50% acetonitrile/: 0.1% (v/v) TFA in water gradient over 12 minutes, 1.6 ml/minute, 225 nm detection). The HPLC chromatographs after 0, 5 and 30 minutes air oxidation are shown in FIG. 5. The shift of the major peak to the peak arrowed being indicative of formation of the 1, 7 disulphide bond. When disulphide bond formation was judged to be complete (30 minutes) the whole of the remaining fraction (1.75 ml) was subjected to an HPLC semi-preparative separation as described above. The purified recombinant hCT-Gly peak was freeze dried and analysed by analytical HPLC, its chromatograph being compared with that of authentic chemically synthesised hCT (FIG. 6). From 44 mg of fusion protein the yield of pure recombinant hCT-Gly was approximately 1.1-2.0 mg corresponding to a theoretical yield for the cleavage step of 19-35%. The predicted amino acid sequence of the purified recombinant hCT-Gly was confirmed by Fast Atom Bombardment (FAB) mass spectrometry analysis.

2) $CAT_I$-Glu-hCT-Gly

A) Preparation of Soluble $CAT_I$-Glu-hCT-Gly Fusion Protein

As described in Example 1 recombinant $CAT_I$-Glu-hCT-Gly fusion protein is produced by E coli HB101/pCT2026 cells as a soluble protein, and thus CAT substrate affinity chromatography was used for recovery and initial purification of the fusion protein. The methods and procedures used for CAT substrate affinity chromatography were essentially as outlined for purification of the native $CAT_I$ enzyme by Bennett and Shaw (Biochem J 215, 29-38, 1983).

E coli HB101 cells containing plasmid pCT2026 were grown at 37° C. to late in the exponential phase of growth in five 1 liter baffled flasks containing 200 ml of a supplemented minimal salts medium with chloramphenicol at 20 μg/ml. The cells (2 g wet weight) were pelleted by centrifugation (10,000 rpm×10 minutes) and cell extract obtained from the pelleted cells by resuspension in 20 ml of 50 mM Tris/HCl, pH 7.8 containing 10 nm EDTA followed by mechanical shearing. The 60° C. heat step described by Bennett and Shaw was omitted. The cell extract was centrifuged (20,000 rpm×20 minutes) and the supernatant was diluted with the above buffer containing 0.1 mM 2-mercaptoethanol. This was then loaded onto the substrate affinity column (50 ml bed volume) which was then washed with the same buffer until the absorbance at 280 nm fell to below 0.02 units. The column was then washed with ten column volumes of the above buffer containing 0.6M NaCl to remove non-specifically bound E coli proteins. The $CAT_I$-Glu-hCT-Gly fusion protein was then eluted from the column with the above buffer containing 0.6M NaCl and 5 mM chloramphenicol.

Chloramphenicol absorbs in the 280 nm region and thus absorbance at this wavelength could not be used to monitor elution of the fusion protein. Instead elution was monitored by measurement of the chloramphenicol acetylating activity of the eluted fractions. The fusion protein was judged to be homogeneous and to be of the predicted size, i.e. approximately 3.5 Kd larger than the native $CAT_I$ protein, by SDS polyacrylamide gel electrophoresis (FIG. 3). The yield of fusion protein obtained was high as determined by assays of chloramphenicol acetylating activity. Subsequent radioimmunoassays using anti-authentic human calcitonin antiserum confirmed the fusion to contain human calcitonin (hCT).

B) Cleavage of $CAT_I$-Glu-hCT-Gly and Purification of hCT-Gly

This fusion protein contains a glutamic acid amino acid residue immediately preceding the hCT-Gly polypeptide sequence and thus the staphylococcal protease was used to cleave the fusion protein and release hCT-Gly polypeptide. The following procedure was used for cleavage.

Column eluate fractions having chloramphenicol acetylating activity as obtained above, were dialysed into 50 mM $NH_4HCO_3$ buffer, pH 7.55 containing 0.1M DTT and 2 mM EDTA. The fusion protein was then mixed with staphylococcal protease (Sigma Product Number P8400) at an enzyme to substrate (w/v) ratio of 1:100 and incubated at 37° C. for 4 hours. On completion of incubation the hCT-Gly polypeptide was purified on an analytical scale by essentially the same purification procedure described above for the purification of hCT-Gly derived from the $CAT_I$-Lys-Arg-hCT-Gly fusion. The hCT-Gly polypeptide obtained from both fusion proteins was found to be indistinguishable by a variety of criteria.

3) Conversion of hCT-Gly to Authentic Human Calcitonin

Subsequent processing of the C-terminal amino acid of the hCT-Gly polypeptide from both fusion protein sources yields the authentic C-terminus of human calcitonin i.e. the proline amide.

4) Stability of CAT-Calcitonin Producing Strains

The strains pCT2024/E coli HB101 and pCT2026/E coli HB101 were grown in a 10 liter fermenter over an extended period of time (about 80 generations) in minimal medium supplemented with chloramphenicol (20 mg/l). The expression levels remained high throughout the induction stage of the fermentation and both plasmids were fully stable to segregation. Additionally plasmid pCT2026 was shown to be completely stable to molecular re-arrangement. (Data not shown).

5) Bioactivity of Human Calcitonin-glycine Polypeptide

The bioactivity of calcitonin-glycine prepared from the CAT$_I$-Lys-Arg-hCT-Gly fusion protein, as described above, was compared with that of authentic human calcitonin using the 50 g rat, intravenous injection protocol described by MacIntyre et al (in 'Handbuch der inneren Medizin VI/1A, Knochen et al, eds, Springer-Verlag, Berlin, 1980, 623–634). The results (FIG. 7) indicate that human calcitonin-glycine exhibits approximately 0.1% of the calcium lowering activity of authentic human calcitonin in 50 g rats. The duration of this lowering activity, however, appears to be longer.

EXAMPLE 3

Use of a CAT-Calcitonin-Glycine Fusion Protein as an Immunogen

Calcitonin is a relatively small polypeptide (32 amino acid residues) and thus is not satisfactory for use on its own as an immunogen for raising antibodies. Therefore the larger CAT-calcitonin-glycine fusion proteins were investigated for use as immunogens for raising antibodies to calcitonin. The CAT$_I$-human calcitonin-glycine fusion protein produced by pAB74/E coli HB101 cells, as described in Example 1 was used as an immunogen. This fusion protein lacks a cleavage site between the CAT$_I$ and human calcitonin-glycine amino acid sequences. Additionally it differs from authentic human calcitonin in that it does not have the correct C-terminal proline amide residue.

CBA/BalbC F1 mice were used to raise antibodies. Mice were immunised with 10 μg aliquots of substrate affinity purified CAT-calcitonin-glycine fusion protein (obtained from cells of E coli HB101 carrying plasmid pAB74) on three consecutive occasions at approximately three week intervals. Sera were taken from the mice approximately 14 days after the second and third immunisations and tested for the presence of antibodies to human calcitonin by a radio-immunoassay procedure. The results for the sera taken after the second immunisation were negative; though after the third immunisation the sera were found to contain appreciable amounts of antibody to human calcitonin.

For the sake of comparison mice were also immunised with 10 μg aliquots of substrate affinity purified native CAT$_I$ protein obtained from cells of E coli C600 containing plasmid pBR328 (Bennett and Shaw supra). Mice were also immunised with 10 μg aliquots of a conventional calcitonin immunogen comprising authentic synthetic human calcitonin cross-linked to ovalbumin carrier protein by glutaraldehyde. The results obtained are given in the Table below indicating that CAT$_I$-hCT-Gly fusion protein elicites a comparable antibody response to a conventional hCT ovalbumin immunogen despite the lack of the strongly immunogenic prolinamide epitope.

TABLE

| hCT Antibody Response in Mice to Various Immunogens | | |
|---|---|---|
| Animal Code | Immunogen | Anti-authentic calcitonin Titre at 1/100 dilution of antisera |
| M0064 - 1 | CAT$_I$ | 0.1% |
| - 2 | CAT$_I$ | 0.1% |
| - 3 | CAT$_I$ | 0.1% |
| - 5 | CAT$_I$ | 0.1% |
| M0065 - 1 | CAT$_I$-hCT-Gly | 3.8% |
| - 2 | CAT$_I$-hCT-Gly | 1.9% average 1.6% |
| - 3 | CAT$_I$-hCT Gly | 0.6% |
| - 5 | CAT$_I$-hCT Gly | 0.2% |
| M0038 - 4 | hCT-ovalbumin | 2.6% average 1.8% |
| M0038 - 1 | hCT-ovalbumin | 1.0% |

It will be appreciated that other CAT fusion proteins, e.g. CAT-ACTH, may also be used as immunogens for raising antibodies. This approach to the raising of antibodies may provide a more economic method for the manufacture of large quantities of immunogens (e.g. for vaccine use) than the conventional synthetic peptide route.

EXAMPLE 4

Construction of CAT$_I$-Calcitonin Fusion Proteins for Production of Asn[15] Human Calcitonin The calcitonin analogue Asn[15] human calcitonin can be made by the chemical amidation of the human calcitonin analogue calcitonin (1–31)+proline. (i.e. the carboxy terminus is proline not prolinamide as in authentic human calcitonin). Asn[15] human calcitonin can then be selectively deamidated to yield authentic human calcitonin.

Plasmid DNA constructs for the expression of the fusion proteins CAT$_I$-lysine-arginine-calcitonin and CAT$_I$-glutamic acid-calcitonin have been made in a analogous manner to those encoding CAT$_I$-lysine-arginine-calcitonin-glycine and CAT$_I$-glutamic acid-calcitonin-glycine. Plasmid D13 (International Patent Application Number WO 84/00380) was digested with BglII and PstI and the fragment encoding the lysine-arginine calcitonin polypeptide was ligated into BglII and PstI digested plasmid pCT202. This gave the chloramphenicol resistance-conferring plasmid pCT2023 (FIG. 1). It is expected that the human calcitonin (1–31) proline polypeptide may be purified from the fusion protein in an analogous manner to the human calcitonin-glycine polypeptide purified from E coli HB101/pCT2024. However in preferred embodiments the host strain would not be E coli HB101 but an E coli strain lacking an amber suppressor mutation. This is because the termination codon used in this construct is the so-called amber termination codon (TAG). Strains carrying an amber suppressor mutation can misread this stop codon as an amino acid codon and hence produce an aberrant, extended fusion protein.

The plasmid pCT2025 which encodes a CAT$_I$-glutamic acid calcitonin fusion protein (FIG. 1) was isolated from pCT2023 by a serios of manipulations which exactly parallel the isolation of pCT2026 from pCT2024. This plasmid also confers chloramphenicol resistance to E coli and, for the reason outlined above, would, in preferred embodiments, be expressed in an E coli host strain lacking an amber suppressor mutation.

The chloramphenicol resistant fusion vector plasmids pCT201, pCT202 and pCT203 as described above in Example 1 were investigated for use in the expression of other foreign polypeptides and proteins in addition to human calcitonin and human calcitonin-glycine. The following examples describe particular experiments which have been carried out, but it will be appreciated that the fusion vector plasmids of the invention are widely applicable for use in the expression of foreign polypeptides and proteins in general.

EXAMPLE 5

Production of CAT$_I$-Met Prochymosin Fusion Protein

A met-prochymosin gene was obtained from the plasmid pCT67 as described by Emtage et al (PNAS Volume 80, Pages 3671-3675, June 1983). The met-prochymosin gene was isolated from pCT67 on a BclI fragment and this fragment was ligated with BglII cut dephosphorylated plasmid pCT202. E coli HB101 cells were transformed with the ligation mix and transformants selected by growth on L-agar containing ampicillin (100 μg/ml). A plasmid, pCT20267, with the correct orientation of the inserted DNA fragment was isolated by EcoRi digestion of small scale plasmid preparations. Strain E coli HB101/pCT20267 was cultured in L-broth growth medium containing 20 μg/ml chloramphenicol. High level expression of an insoluble protein, which was judged by SDS polyacrlylamide gel electrophoresis to be the expected size for the CAT$_I$-met prochymosin fusion protein, was obtained, Cell extracts from E coli HB101/pCT20267 were subsequently shown to be immunoreactive with rabbit anti-chymosin antiserum.

This insoluble protein is solubilised and acid treated to yield authentic calf chymosin. For instance the insoluble protein may solubilised in concentrated urea solution and subsequent acid treatment may yield authentic calf chymosin.

EXAMPLE 6

Production of CAT$_I$-ACTH Fusion Protein

A synthetic gene, with E coli optimised codons, and which when ligated into an appropriate vector codes for a polypeptide consisting of amino acid residues $-1$ to $+14$ if ACTH was prepared. Six synthetic oligonucleotides were obtained.

| R242 | 5' GAACACTTCCGTTGGGGTA 3' |
| R243 | 5' GATCTTACTCTATG 3' |
| R244 | 5' AACCTGTTGGTTGATCAGA 3' |
| R245 | 5' GAAGTGTTCCATAGAGTAA 3' |
| R246 | 5' CAACAGGTTTACCCCAACG 3' |
| R247 | 5' AGCTTCTGATCAAC 3' |

Oligonucleotides R242, R244, R245, R246 and R247 were phosphorylated and were added to R243 and all mixed in excess with BglII/HindIII cut plasmid pCT202. The resultant plasmid mixture after ligation was transformed into E coli HB101 cells and E coli HB101/pCATACTH transformants were selected by growth on medium containing 100 μg/ml ampicillin. The E coli HB101/pCATACTH cells were cultured to late in the exponential phase of growth in supplemented minimal salts medium containing 20 μg/ml chloramphenicol and gave high level expression of a partially soluble fusion protein having the predicted size, as judged by SDS polyacrylamide gel electrophoresis.

The purified CAT-ACTH fusion protein was recovered and purified by ion exchange by chromatography. Similarly, as for the CAT-hCT-Gly fusion protein, the CAT-ACTH fusion protein is suitable for use as an immunogen for raising antibodies to ACTH.

Similarly fusion protein vectors have been constructed for expression of CAT-Foot and Mouth Disease Virus (FMDV) antigenic peptide fusion protein and for CAT-calcitonin fusion protein containing other cleavage sites besides the Lys-Arg and glutamic acid cleavage sites discussed above, e.g. a blood coagulation factor $X_a$ site.

We claim:

1. A process for the production of a fusion protein comprising a eucaryotic polypeptide linked to the carboxy terminus of an active portion of a chloramphenicol acetyltransferase (CAT) protein, the process comprising culturing a host organism transformed with a vector including a gene coding for the fusion protein to obtain expression of the gene, and isolating the fusion protein.

2. A process for the production of a eucaryotic polypeptide comprising producing a fusion protein comprising a eucaryotic polypeptide linked to the carboxy terminus of an active portion of a chloramphenicol acetyltransferase (CAT) protein by culturing a host organism transformed with a vector including a gene coding for the fusion protein to obtain expression of the gene, cleaving the fusion protein and isolating the eucaryotic polypeptide.

3. A process according to claim 1 or 2 wherein the fusion protein is isolated by affinity chromatography using a solid phase to which is bound a substrate to which the active portion of the CAT protein is capable of specifically binding.

4. A process according to claim 1 or 2 wherein the host organism is a bacterium and the culture medium includes chloramphenicol or a bacteriocidal analogue thereof.

5. A process according to claim 2 in which, after cleavage of the fusion protein in solution, the pH of the solution is adjusted to a level effective to cause precipitation of the active portion of the CAT protein, leaving the eucaryotic polypeptide in solution, and the polypeptide is isolated.

6. A process according to claim 2, in which the polypeptide is linked to the active portion of the CAT protein through a linkage capable of selective chemical or enzymatic cleavage.

7. A process according to claim 6, in which the linkage is a glutamic acid amino acid residue.

8. A process according to claim 6, in which the linkage is a lysine arginine peptide residue.

9. A process according to claim 7 comprising cleaving the fusion protein at the glutamic acid amino acid residue with staphylococcal protease.

10. A process according to claim 8 comprising cleaving the fusion protein at lysine-arginine with clostripain.

11. A DNA sequence coding for a fusion protein comprising a eucaryotic polypeptide linked to the carboxy terminus of an active portion of a chloramphenicol acetyltransferase (CAT) protein.

12. A DNA sequence according to claim 11, in which the polypeptide is linked to the active portion of the CAT protein through a linkage capable of selective chemical or enzymatic cleavage.

13. A vector including a DNA sequence according to claim 11.

14. A host organism transformed with a vector according to claim 13.

15. A process for the production of a fusion protein comprising a heterologous polypeptide linked to the carboxy terminus of an active portion of a chloramphenicol acetyltransferase (CAT) protein, the process comprising culturing a host organism transformed with a vector including a gene coding for the fusion protein to obtain expression of the gene, and isolating the fusion protein, wherein the fusion protein is selected from the group consisting of: CAT-adenocortitrophic hormone, CAT-met prochymosin, and CAT-calcitonin fusion proteins.

16. A process according to claim 15, wherein the fusion protein is a CAT-adenocortitrophic fusion protein.

17. A process according to claim 15, wherein the fusion protein is a CAT-met prochymosin fusion protein.

18. A process according to claim 15, wherein the fusion protein is a CAT-calcitonin fusion protein.

19. A process for the production of a polypeptide comprising the steps of producing a fusion protein comprising an active portion of a chloramphenicol acetyltransferase (CAT) protein and a polypeptide by culturing a host organism transformed with a vector including a gene coding for the fusion protein to obtain expression of the gene, cleaving the fusion protein and isolating the polypeptide, wherein the polypeptide is selected from the group consisting of: calcitonin, chymosin and adenocortitrophic hormone polypeptides.

20. A process according to claim 19, wherein said polypeptide is a calcitonin polypeptide.

21. A process according to claim 19, wherein said polypeptide is a chymosin polypeptide.

22. A process according to claim 19, wherein said polypeptide is an adenocortitophic hormone polypeptide.

* * * * *